(12) United States Patent
Hayden et al.

(10) Patent No.: US 10,031,109 B2
(45) Date of Patent: Jul. 24, 2018

(54) OPTOACOUSTIC INSPECTION DEVICE FOR INSPECTION OF SEMICONDUCTOR WAFERS

(75) Inventors: Chanel Moira Pia Hayden, Dublin (IE); Patrick J. McNally, Dublin (IE); Stephen Daniels, Dublin (IE)

(73) Assignee: DUBLIN CITY UNIVERSITY, Glasnevin, Dublin (IE)

( * ) Notice: Subject to any disclaimer, the term of this patent is extended or adjusted under 35 U.S.C. 154(b) by 1384 days.

(21) Appl. No.: 13/879,340

(22) PCT Filed: May 18, 2011

(86) PCT No.: PCT/EP2011/058089
§ 371 (c)(1),
(2), (4) Date: Jun. 7, 2013

(87) PCT Pub. No.: WO2012/052193
PCT Pub. Date: Apr. 26, 2012

(65) Prior Publication Data
US 2013/0247658 A1    Sep. 26, 2013

(30) Foreign Application Priority Data
Oct. 18, 2010 (GB) .................... 1017560.2

(51) Int. Cl.
*G01N 29/04* (2006.01)
*G01N 21/17* (2006.01)
(Continued)

(52) U.S. Cl.
CPC ....... *G01N 29/041* (2013.01); *G01N 21/1702* (2013.01); *G01N 29/14* (2013.01);
(Continued)

(58) Field of Classification Search
CPC .. G01N 21/1702; G01N 29/14; G01N 29/041; G01N 29/2418; G01N 29/27;
(Continued)

(56) References Cited

U.S. PATENT DOCUMENTS

| | | | |
|---|---|---|---|
| 4,683,750 A | 8/1987 | Kino et al. | |
| 5,085,080 A * | 2/1992 | Yu ..................... | G01H 13/00 374/E11.011 |

(Continued)

OTHER PUBLICATIONS

D Schneider et al: "Non-destructive testing of damage layers in GaAs wafers by surface acoustic waves" Semiconductor Science and Technology, IOP Publishing LTD: Jan. 1, 1999: pp. 93-98.

*Primary Examiner* — Lisa Caputo
*Assistant Examiner* — Tarun Sinha
(74) *Attorney, Agent, or Firm* — Brundidge & Stanger, P.C.

(57) ABSTRACT

An inspection device is provided which comprises a receiving member defining an open cell for receiving a target therein. An optical excitation input is in optical communication with the cell for exciting the target. At least one acoustic pickup is in acoustic communication with the cell for picking up acoustic energy resultant from excitation of the target. A recorder is provided for recording the acoustic energy picked up from the at least one acoustic pickup for facilitating structural analysis of the target.

34 Claims, 11 Drawing Sheets

(51) Int. Cl.
  *G01N 29/14* (2006.01)
  *G01N 29/24* (2006.01)
  *G01N 29/27* (2006.01)

(52) U.S. Cl.
  CPC ......... *G01N 29/2418* (2013.01); *G01N 29/27* (2013.01); *G01N 2291/0232* (2013.01); *G01N 2291/0289* (2013.01); *G01N 2291/2632* (2013.01)

(58) Field of Classification Search
  CPC ... G01N 2291/0232; G01N 2291/0289; G01N 2291/2632
  USPC .......................................................... 73/643
  See application file for complete search history.

(56) References Cited

U.S. PATENT DOCUMENTS

| | | | | |
|---|---|---|---|---|
| 7,345,766 B2* | 3/2008 | Schindler | ........... | G01N 21/1702 356/437 |
| 2005/0188389 A1* | 8/2005 | Namiki | ................. | G11B 17/03 720/610 |
| 2007/0214464 A1* | 9/2007 | Nakada | ................. | G11B 33/02 720/651 |
| 2010/0045998 A1* | 2/2010 | Fritz | ................. | G01N 21/1702 356/450 |
| 2010/0053618 A1* | 3/2010 | Nakajima | ............ | A61B 5/0059 356/432 |
| 2010/0094561 A1* | 4/2010 | Masumura | ........... | A61B 5/0073 702/19 |

* cited by examiner

OPTOACOUSTIC INSPECTION DEVICE FOR INSPECTION OF SEMICONDUCTOR WAFERS

FIELD OF THE INVENTION

The present invention relates to an inspection device. In particular the invention relates to an inspection device which utilises sound energy resultant from light excitation of a target to perform structural characterisation thereof.

BACKGROUND

Failure analysis of semiconductor wafers is the process of collecting and analysing data to determine the cause of a failure within materials, structures, devices and circuits fabricated thereon. Such analysis provides vital information when developing new products and improving existing products. Typically, this type of analysis relies on collecting failed components for subsequent examination of the cause of failure using various methods, such as microscopy and spectroscopy. The disadvantage of this approach is that the analysis is not carried out in real time during the manufacturing process which may result in a large number of faulty devices being manufactured before detection.

There is therefore a need for an inspection device which addresses at least some of the drawbacks of the prior art.

SUMMARY

These and other problems are addressed by provision of an inspection device which utilises sound energy resultant from light excitation of a target to perform structural characterisation thereof.

Accordingly, a first embodiment provides an inspection device as detailed in claim 1. The application also relates to an inspection assembly as detailed in claim 44. Advantageous embodiments are provided in the dependent claims.

These and other features will be better understood with reference to the followings Figures which are provided to assist in an understanding of the present teaching.

BRIEF DESCRIPTION OF THE DRAWINGS

The present teaching will now be described with reference to the accompanying drawings in which.

DETAILED DESCRIPTION OF THE DRAWINGS

The application will now be described with reference to some exemplary inspection devices which are provided to assist in an understanding of the present teaching.

Figure 1:
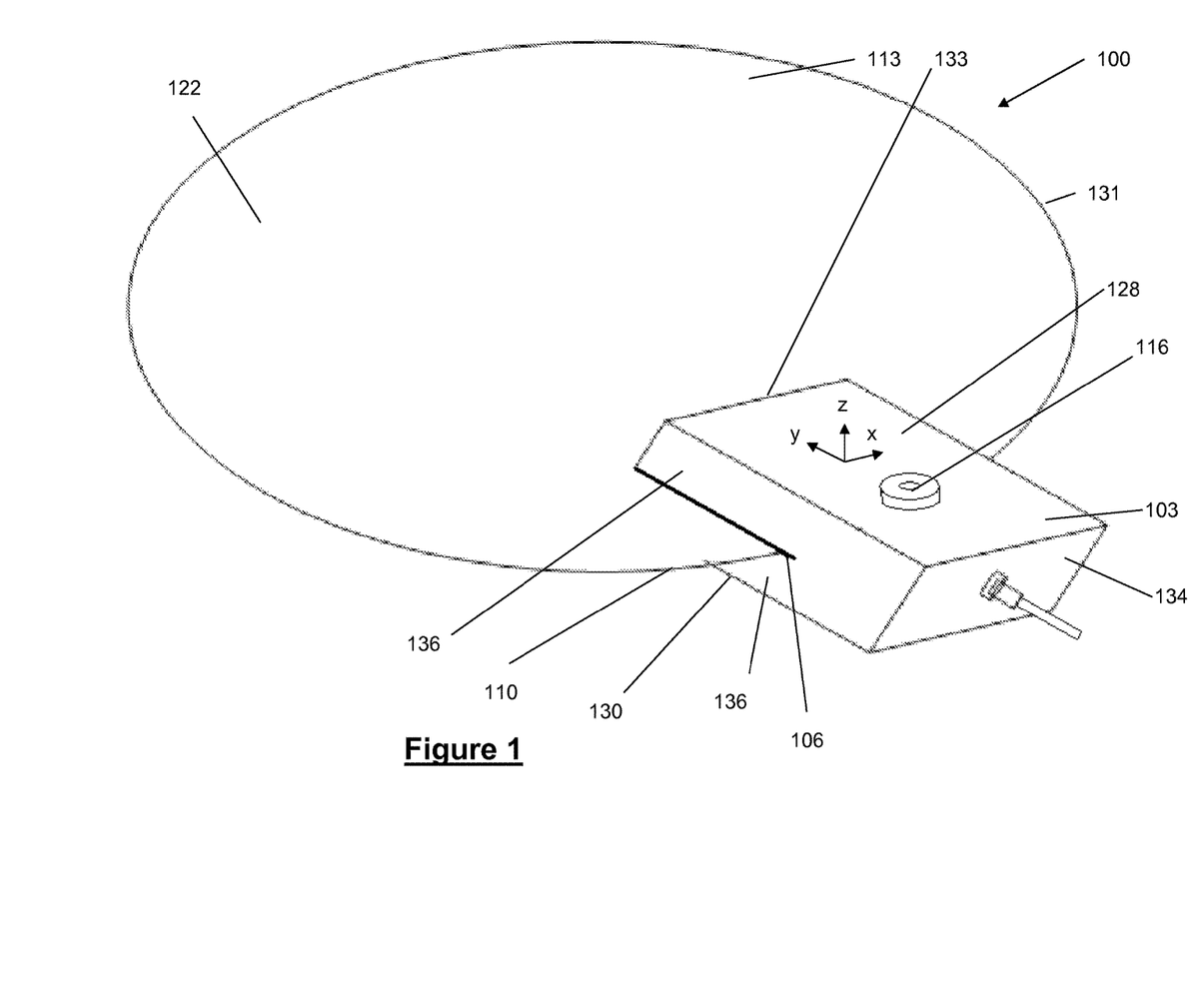
FIG. 1 is a perspective view of an inspection device.

Referring to the drawings and initially to FIG. 1 there is provided an inspection device 100 which utilises sound energy resultant from light excitation of a target to perform structural characterisation thereof. The device 100 comprises a bifurcated receiving member 103 which defines an open cell 106 for receiving a target, in this case, a portion of a semiconductor wafer 113 therein. An optical excitation input 116 is provided on the receiving member 103 which is in optical communication with the cell 106 for exciting the wafer 113. One or more acoustic pickups 118 are provided on the receiving member 103 which are in acoustic communication with the cell 106 for picking up acoustic energy resultant from excitation of the wafer 113. While the exemplary teaching will be described with reference to the targets being semiconductor wafers, it will be appreciated that an inspection device in accordance with the present teaching may be used with a variety of different target types and dimensions—and indeed whole or part of individual targets. For example, the target may be a whole or partial substrate and may be carried on a carrier member if desired. It is not intended to limit the target to any particular shape or size.

The optical excitation input 116 provides a laser source 124 capable of providing a variable wavelength output which is focused and scanned across a target region 125 on an upper major surface 122 of the wafer 113. Light from the light source 124 enters the cell 106 through a transparent window 123 and is intensity-modulated at a predetermined frequency. The wafer 113 moves in a controlled manner relative to the laser source 124, desirably through effecting a rotation of the wafer relative to the laser source, such that the laser source 124 scans the target region 125. Some light is absorbed by the wafer 113 on or close to the surface 122 causing periodic surface heating to occur at the modulation frequency. The periodic surface heating in the wafer 113 provides a source of thermal waves that propagate from the target region 125. This periodic heating causes a periodic pressure variation which is picked up by the acoustic pick up 118. As the modulation frequency is related to the thermal diffusion length of the wafer material, various depths within the wafer 13 can be probed. A visible spectrum may be obtained by determining the acoustic signal of the wafer 113 as a function of the wavelength and modulation frequency of the incident light source 124.

Figure 2:
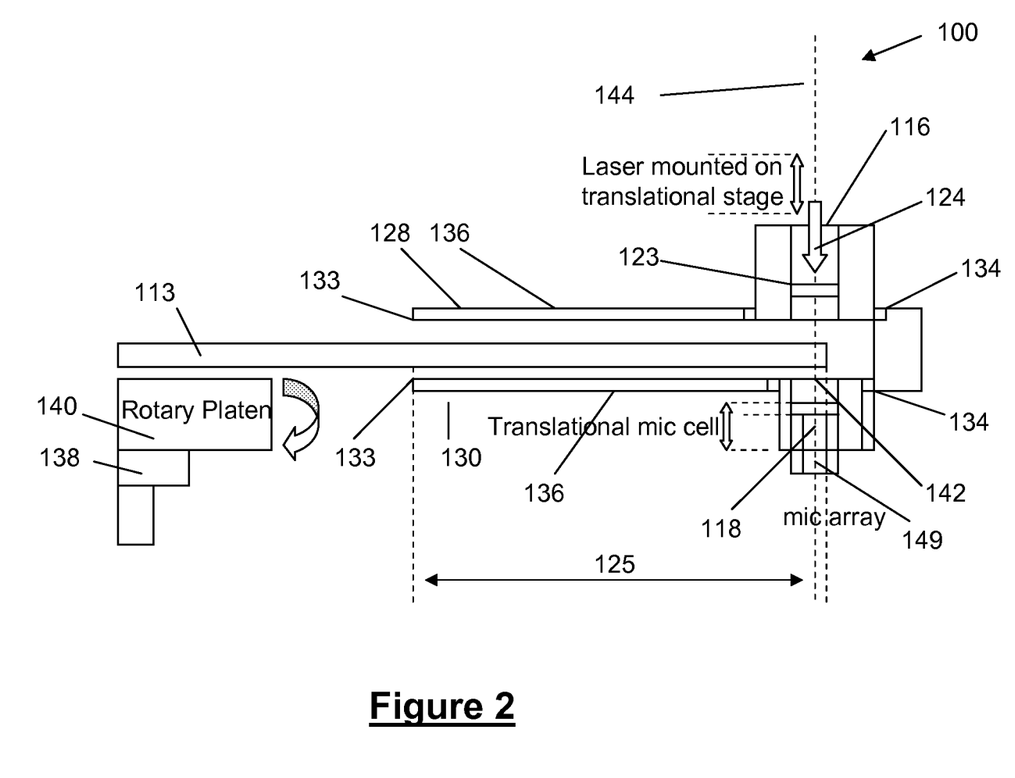
FIG. 2 is a side cross sectional view of the device of FIG. 1.

The receiving member 103 comprises an upper jaw 128 and a spaced apart lower jaw 130 defining a mouth therebetween for receipt of a wafer. The upper and lower jaws are operable coupled together at their respective proximal ends which together define an internal arcuate surface for accommodating the circular edge 131 of the wafer 113. The cell 106 defines a volume or hollow region between the upper jaw 128 and lower jaw 130, of sufficient dimension for accommodating the wafer. The respective jaws are rectangular when viewed in plan elevation. Each jaw comprises a distal end 133 and a proximal end 134 with sides 136 extending there between.

In the exemplary embodiment, the upper jaw 128 has a length of 90 mm at the centre and 81.5 mm at the edge, a width of 100 mm and a depth of 11 mm. The lower jaw 130 has a length of 90 mm at the centre and 81.5 mm at the edge, a width of 100 mm and a depth of 35 mm. The dimensions of the jaws are provided by way example only and it is not intended to limit the scope to particular dimensions. The hollow region between the jaws is open adjacent the distal ends 133 and the sides 136. The proximal ends 134 of the jaws are closed. It will therefore be appreciated that access to the cell 106 is via the distal ends 133 and the two spaced apart sides 136. The arrangement of the jaws whereby the cell 106 is accessible from three sides is particularly advantageous for facilitating loading the wafer 113 or a carried member therein.

The target region 125 of the wafer 113 is defined by the portion of the wafer 113 received in the cell between the upper jaw 128 and the lower jaw 130. In an exemplary embodiment, the distance between the upper jaw 128 and the lower jaw 130 may be varied. Thus the dimensions of the cell 106 may in turn be varied. The receiving member 103 may be provided in a modular arrangement for facilitating altering the dimensions of the cell 106. Alternatively, the receiving member 106 may include a plurality of cells 106 with at least two cells having different dimensions. Such a multiple cell arrangement is particularly advantageous for accommodating wafers or carrier members of various dimensions.

A loading mechanism 138 is configured for loading the target region 125 of the wafer 113 into the cell 106 via the three open sides of the receiving member 103. The loading mechanism 138 includes a centrifuge 140 for rotating the wafer 113. The centrifuge may be configured to provide a constant speed of rotation or may alternatively be configured to allow the speed of rotation to be varied throughout the test process to allow more time to be spent testing specific regions of the target wafer. The loading mechanism 138 loads the wafer 113 to the receiving member 103 such that the upper major surface 122 thereof is co-planar with a horizontal plane. The target region 125 is spaced apart from the respective jaws and is free from contact. It will be appreciated that the target region 125 of the wafer 113 continually changes as the wafer 113 revolves 360° on the motorised stage of the centrifuge 140. In addition, the position of the light source 124 may be rastered/scanned radially inwards and outwards or indeed azimuthally if required to ensure full coverage of the wafer 113. In the exemplary embodiment the rastering/scanning could be performed using a galvanometer scanner.

Figure 3:
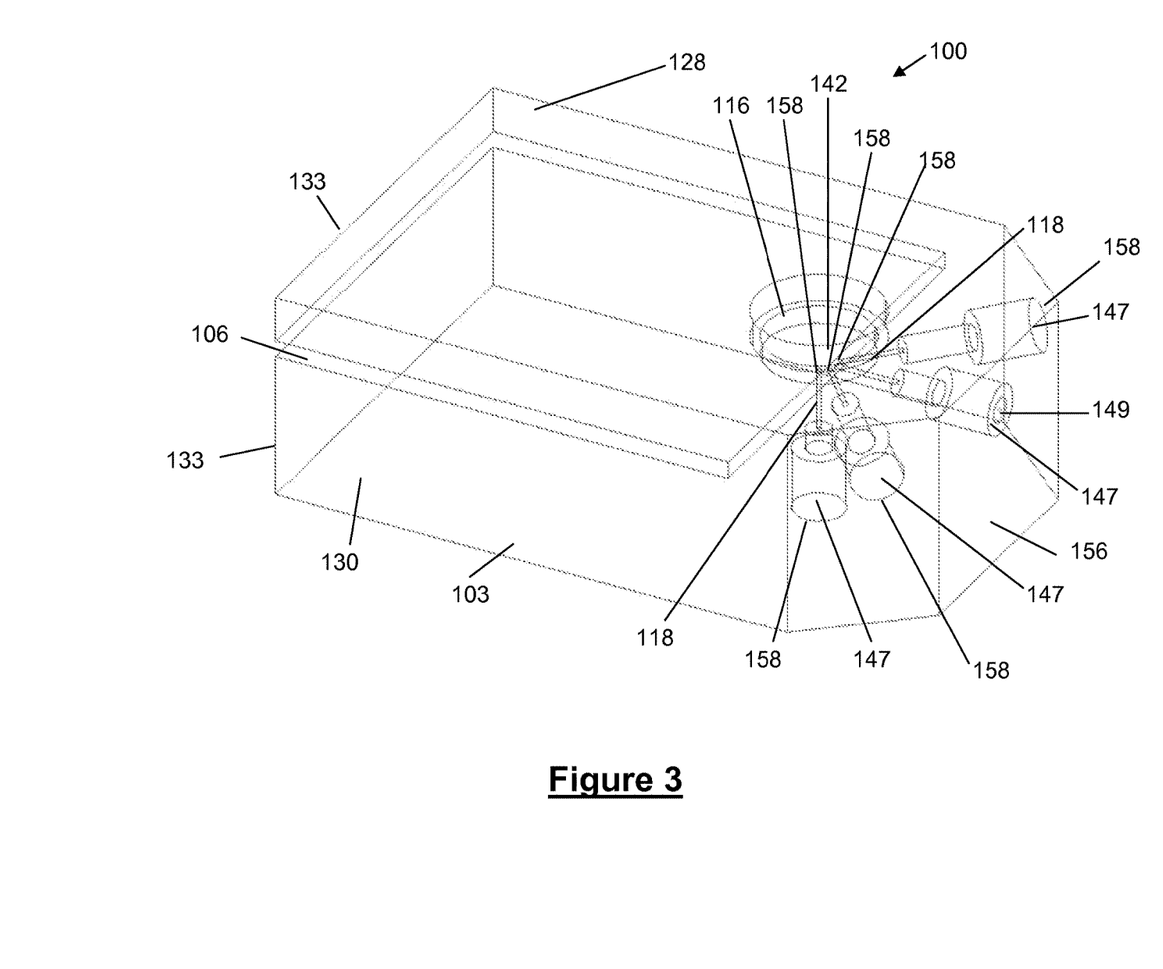
FIG. 3 is a perspective view of an inspection device.
Figure 4:
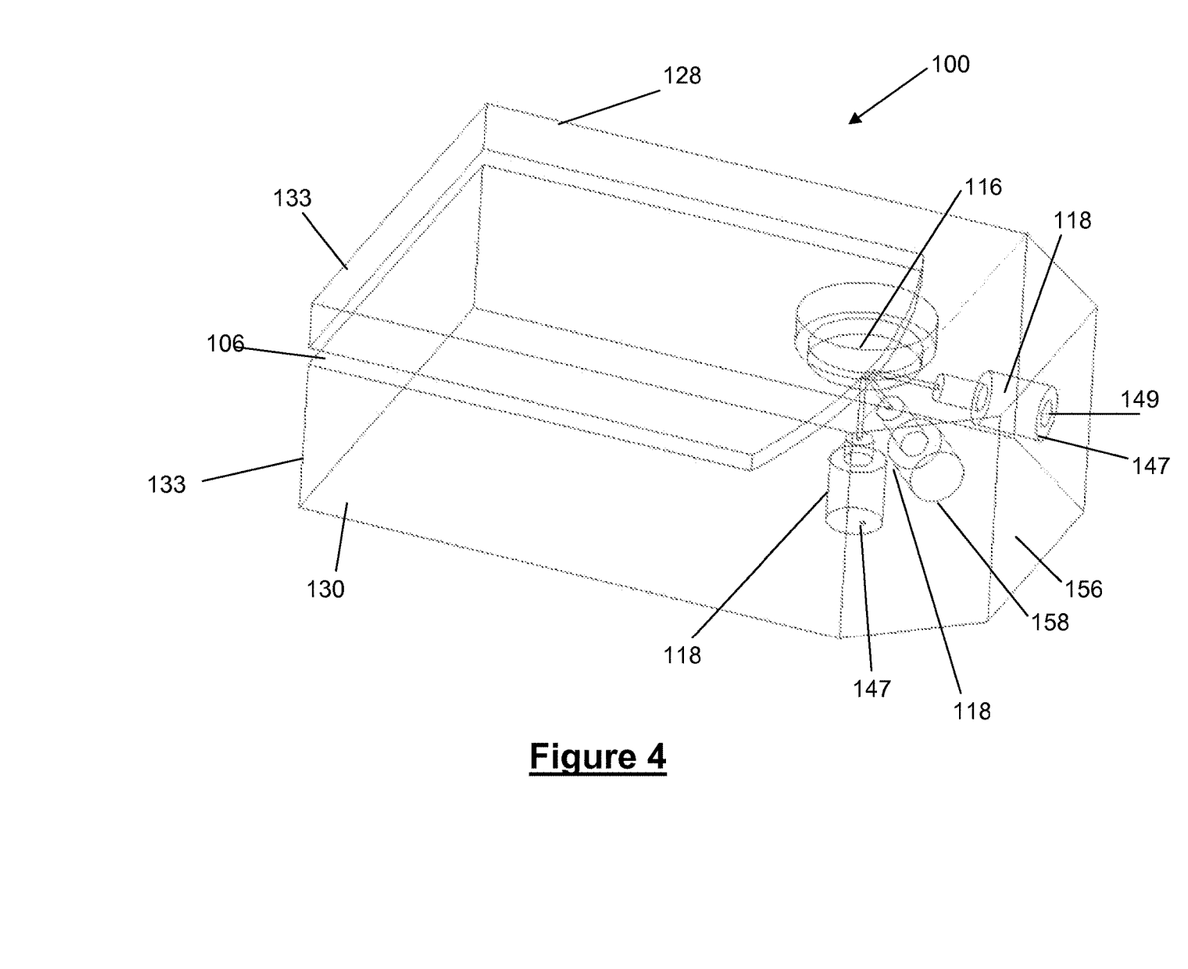
FIG. 4 is a perspective view of an inspection device.
Figure 5:
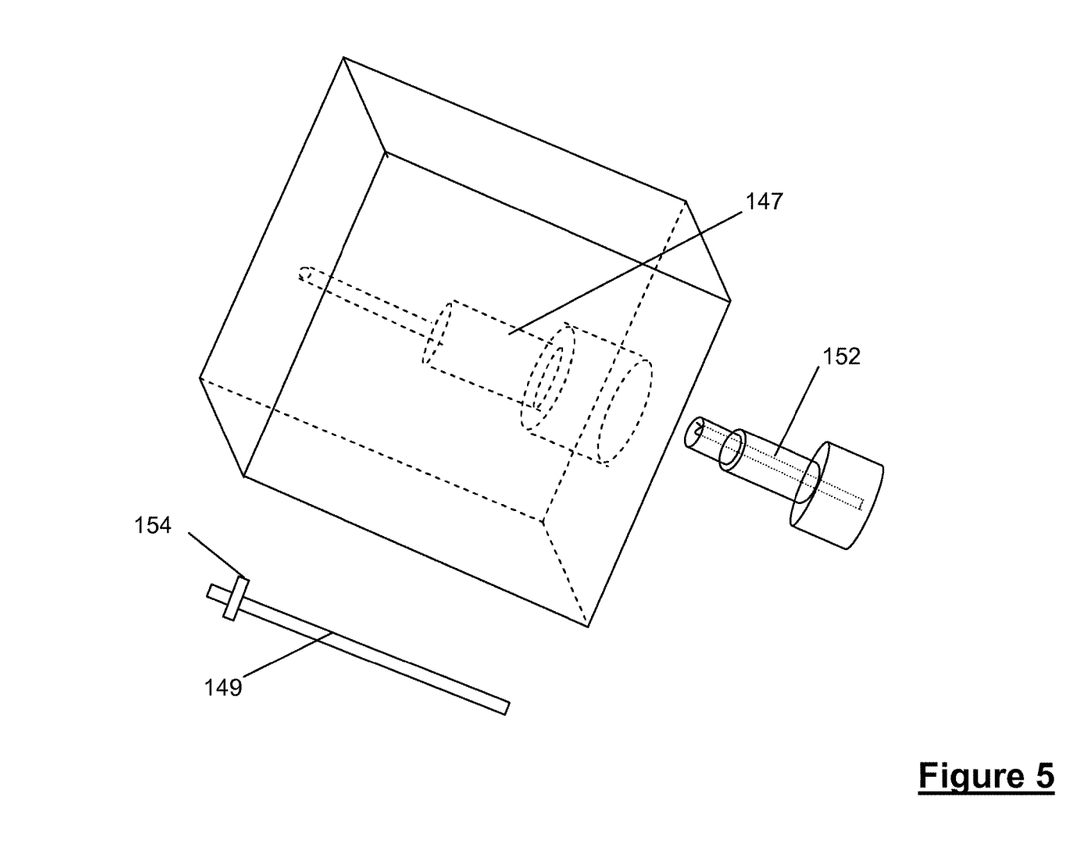
FIG. 5 is a diagrammatic view of a detail of an inspection device.

The light from the light source 124 is focused on a target point 142 on the lower jaw 130. The input 116 is in registration with the target point 142 so that they are aligned relative to a vertical axis 144. In the exemplary embodiment, a plurality of acoustic pick ups 118 are formed in the receiving member 103 as illustrated in FIGS. 3 and 4. Each acoustic pick up 118 comprises an acoustic channel 147 formed on the receiving member 103 and dimensioned for accommodating a microphone 149 therein. The acoustic channels 147 are of circular cross section with a diameter that progressively increases from the target point 142. The acoustic channels 147 in this exemplary arrangement are machined into the underside and backside of the receiving member 103 and facilitate acoustic signals to be received from a variety of locations in the cell 106. The acoustic channels 147 are formed to give acoustic resonance. The channel volume may be varied and the modulation frequency tuned to produce an acoustic resonance by moving a suitable microphone 149 housing in and out of the acoustic channel 147. The microphones 147 are housed in a machined acetal or similar tubular member 152 and sealed on one side. The tubular member 152 may be inserted into an acoustic channel 147 where a suitably sized O-ring 154 prevents sound escaping around the perimeter of the tubular member 152. The O-ring 154 sealably engages the tubular member 152 housing the microphone 149 into a respective acoustic channel 147. The acoustic channels 147 extend radially from the target point 142 on the lower jaw 130 to a rear wall 156 of the receiving member 103. Entrance ports 158 communicate the acoustic channels 147 with the cell 106. The entrance ports 158 are located equidistance from the target point 142. The volume of the acoustic channels may be modified by varying the distance by which the tubular members 152 are inserted into the acoustic channels 147. The tubular members 152 and the acoustic channels 147 define a complimentary interengageable formation in the form of a plug and socket arrangement. External access to the acoustic channels 147 is provided via apertures 158 on the rear wall 156 of the receiving member 103. Electrical connections to the microphones 149 may be made via the apertures 158 which electrically couple the microphones 149 to a pre-amplification circuit 160.

Figure 6:
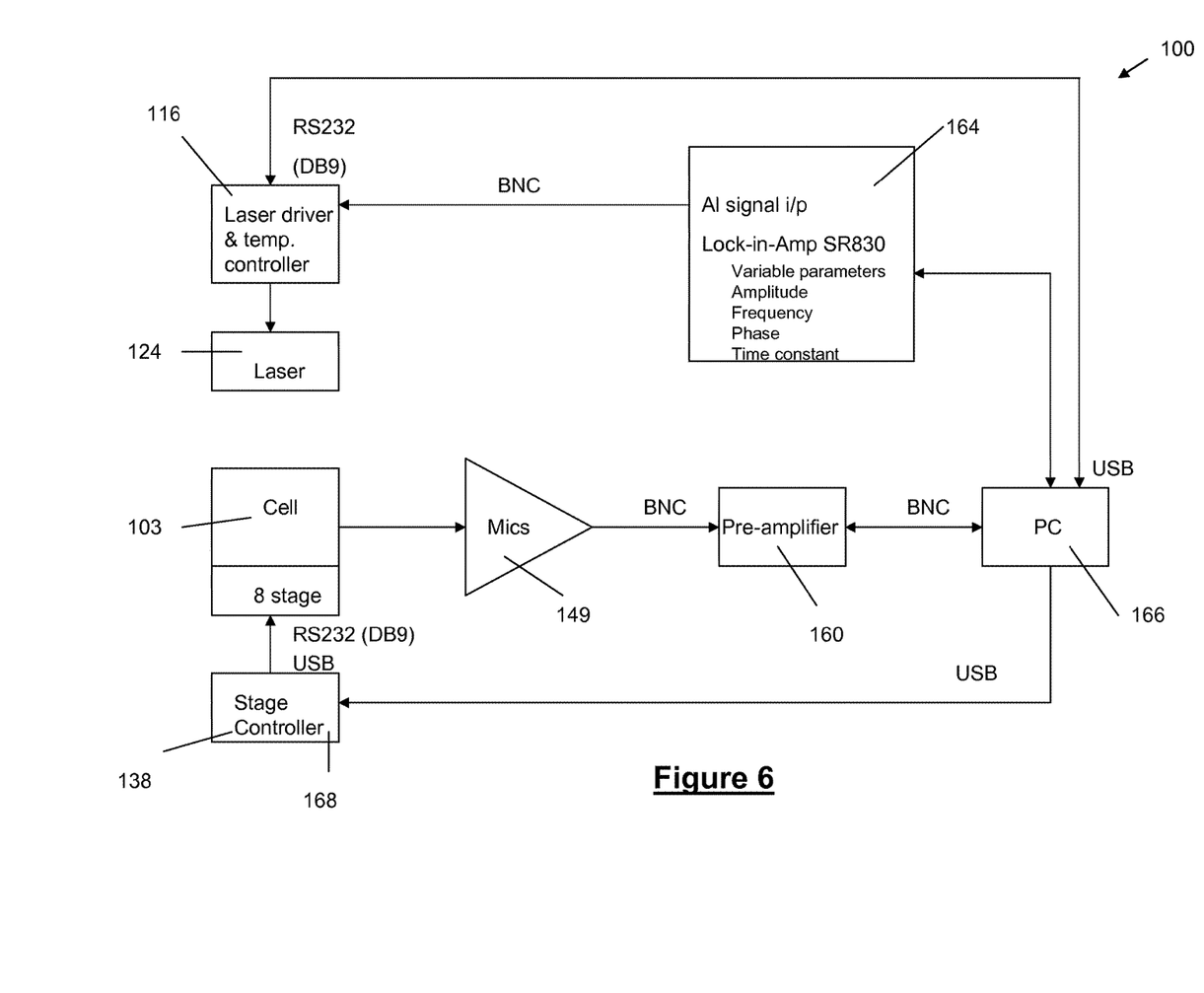
FIG. 6 is a schematic view of a circuit for use in the control of an inspection device.
Figure 7:
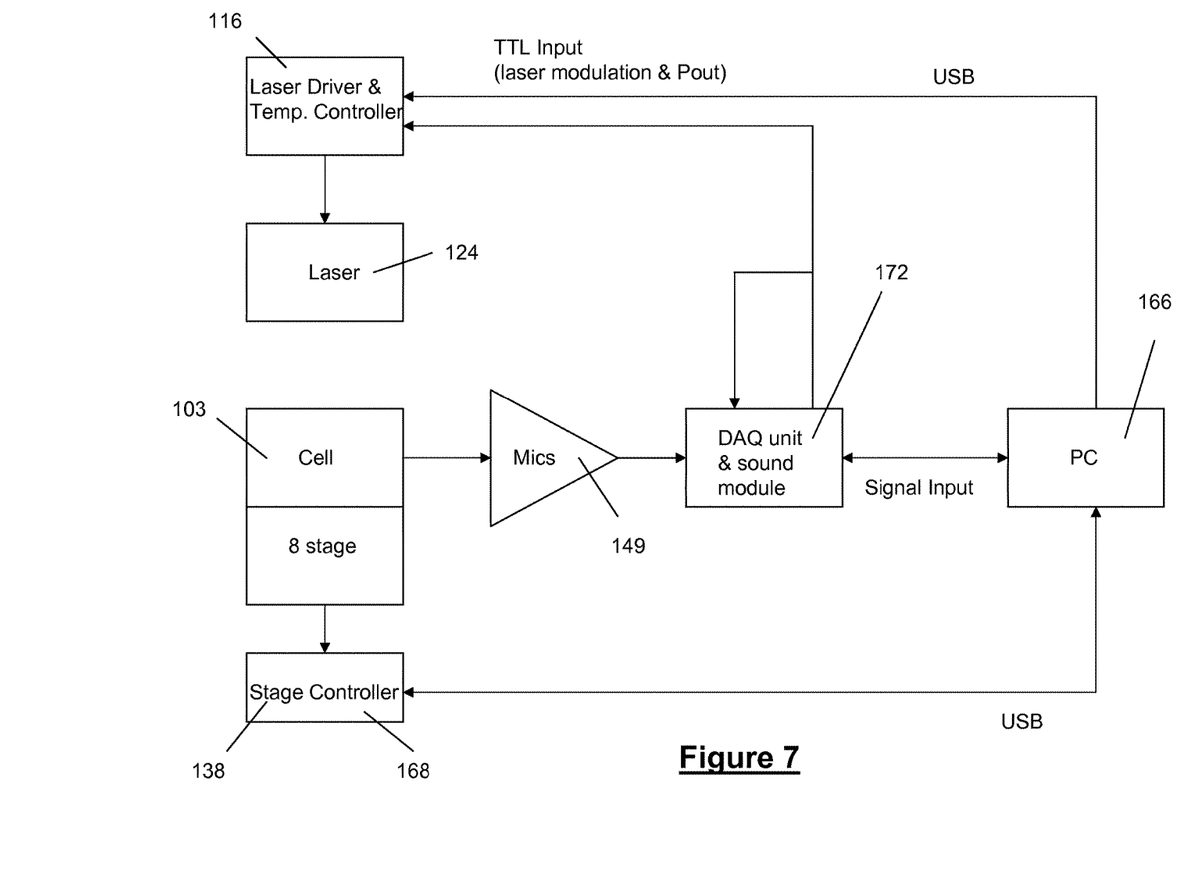
FIG. 7 is a schematic view of a circuit for use in the control of an inspection device.

An exemplary device 100 which uses a lock-in-amplifier set-up is illustrated in FIG. 6. A computer 166 is configured to send and receive commands from a positioning controller 168 of the loading mechanism 138 which manoeuvres the wafer 113 such that the wafer moves relative to the laser source 124. The wafer 113 is loaded into the cell 106 such that the target region 125 is not contacting any other component. Acoustic signals are detected when the wafer 113 is illuminated by light from the laser source 124 whose modulation frequency is provided by a TTL signal from the lock-in-amplifier 164. The acoustic signal is picked up by sensitive microphones 149 in the acoustic channels 147 which are connected to the pre-amplifier circuit 160. The computer 166 is operably coupled to the pre-amplifier circuit 160 and the lock-in-amplifier 164 which records the amplitude and phase of the signal. This information may then be recorded on the computer 166 using customised software through a general purpose interface bus connection. The lock-in-amplifier 164 is an amplifier which is operable to detect a periodic signal in a noisy environment. It is essentially a homodyne system combined with a narrow low pass filter where the detected signal is mixed with a known reference signal. Using this mixing the lock-in amplifier 164 can convert the signal's amplitude and phase to a low-frequency voltage signal, which is passed through the very narrow low pass filter. The operation of lock-in-amplifiers is well known in the art, and it is not intended to describe their operations further. An alternative circuit arrangement which is substantially similar to the circuit of FIG. 6 is illustrated in FIG. 7. The main difference is that the lock-in-amplifier 164 of FIG. 6 is replaced by a software lock-in-amplifier and a data acquisition (DAQ) unit 172 which houses sound modules and digital output modules for controlling the optical input 116.

Figure 8:
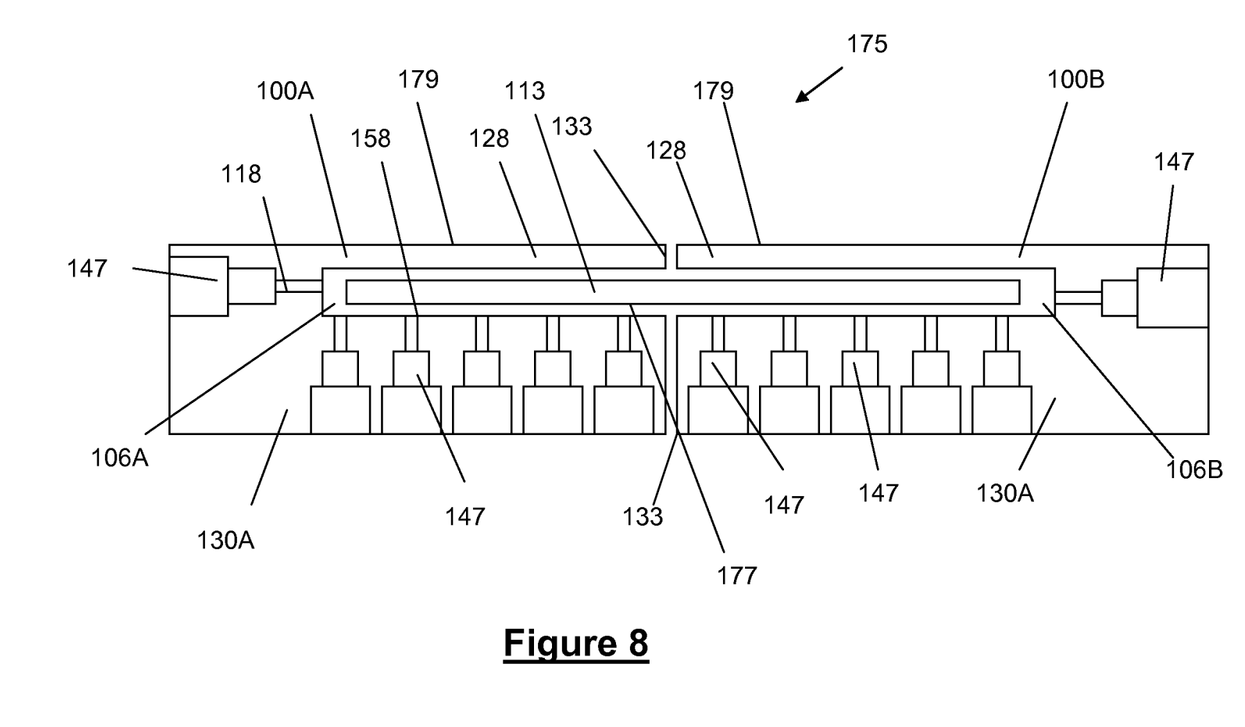
FIG. 8 is a side cross sectional view of an assembly including two inspection devices.

Referring now to FIG. 8, which shows an inspection assembly 175 that includes two devices 100A and 100B located opposite each other and aligned vertically and horizontally. The devices 100A and 100B are aligned such that the respective distal ends 133 are in registration. The cell 106A and the cell 106B together define an access slot 177 which may be fed continuously with wafers 113. The wafers 113 may be loaded from one side 136 of the receiving members 103 and moved through the slot 177 for exiting on the opposite side thereof. The assembly 175 is particularly advantageous for facilitating the feeding of a plurality of wafers in a continuous fashion through the slot 177. The receiving members 103A and 103B each includes an oblong window 179 which extends along the length of the upper jaw 128 which facilitates scanning a laser beam 124 across the wafer 113 while multiple microphones 149 on the lower jaws 130 detects the resultant acoustic signal.

Figure 9:
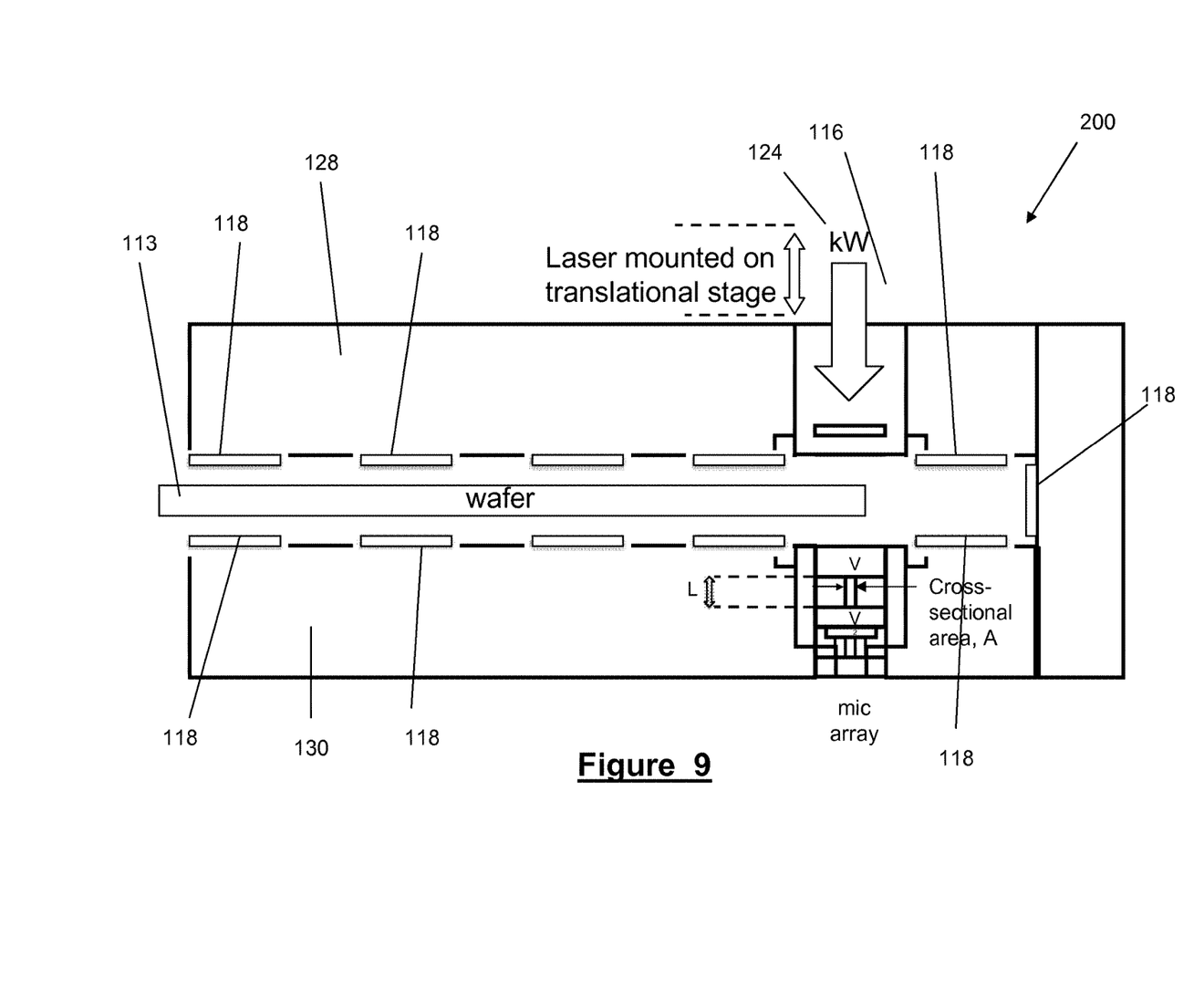
FIG. 9 is a diagrammatic view of another inspection device.

Referring now to FIG. 9, which illustrates another embodiment of an inspection device 200. The device 200 is substantially similar to the device 100 and like components are identified by similar reference numerals. The main difference between the device 200 and the device 100 is that in device 200 the acoustic pick-ups 118 are provided above and below the wafer 113. Acoustic pick-ups 118 may also be provided adjacent the edge 131 of the wafer 113. By providing acoustic pick-ups above, below and at the edge of the wafer it is possible to optimize acoustic signal capture. Also the arrangement facilitates differential analysis i.e. one set of acoustic signals may be subtracted from another set of acoustic signals, for example, the reflected/top microphone signals may be subtracted from the bottom/transmitted signals, in order to enhance signal-to-noise ratios. The differential analysis may be performed electronically and optimized for the unique conditions of the particular target material under test. In addition, two or more adjacent devices could be used, one of which uses no laser/light source stimulation thereby detecting the background/ambient signal, which defines the systemic noise level. This signal data may be subtracted electronically from the detected signals in the adjacent device, which utilizes the light source. Such a methodology may be used to enhance signal to noise ratios.

Figure 10:
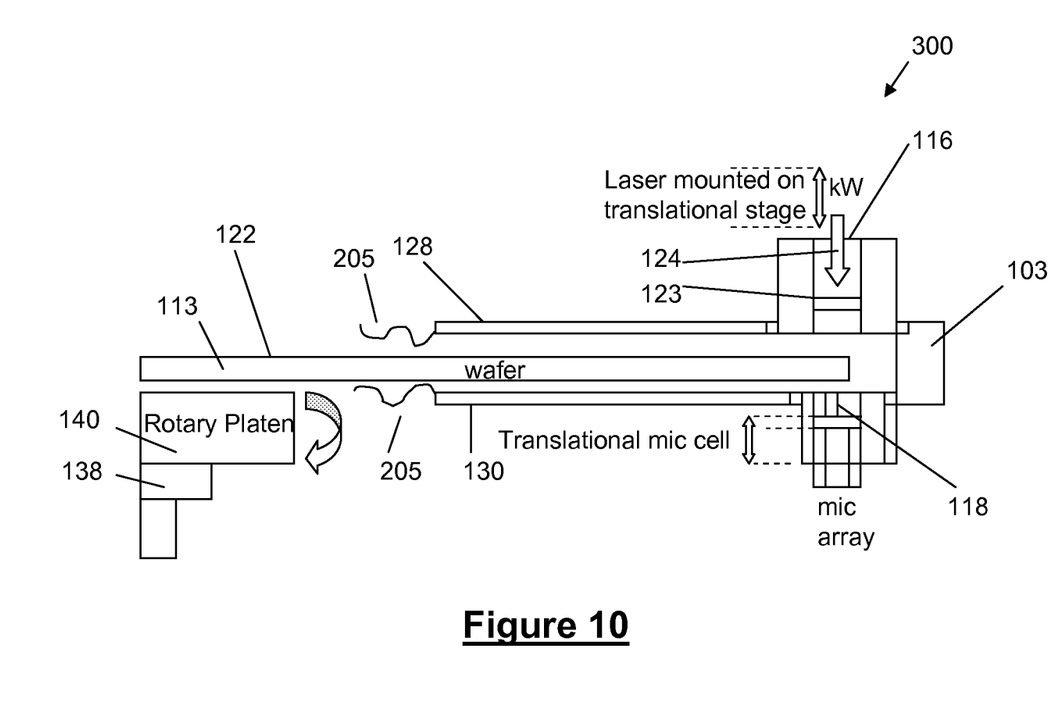
FIG. 10 is a diagrammatic view of a further inspection device.
Figures 11, 12:
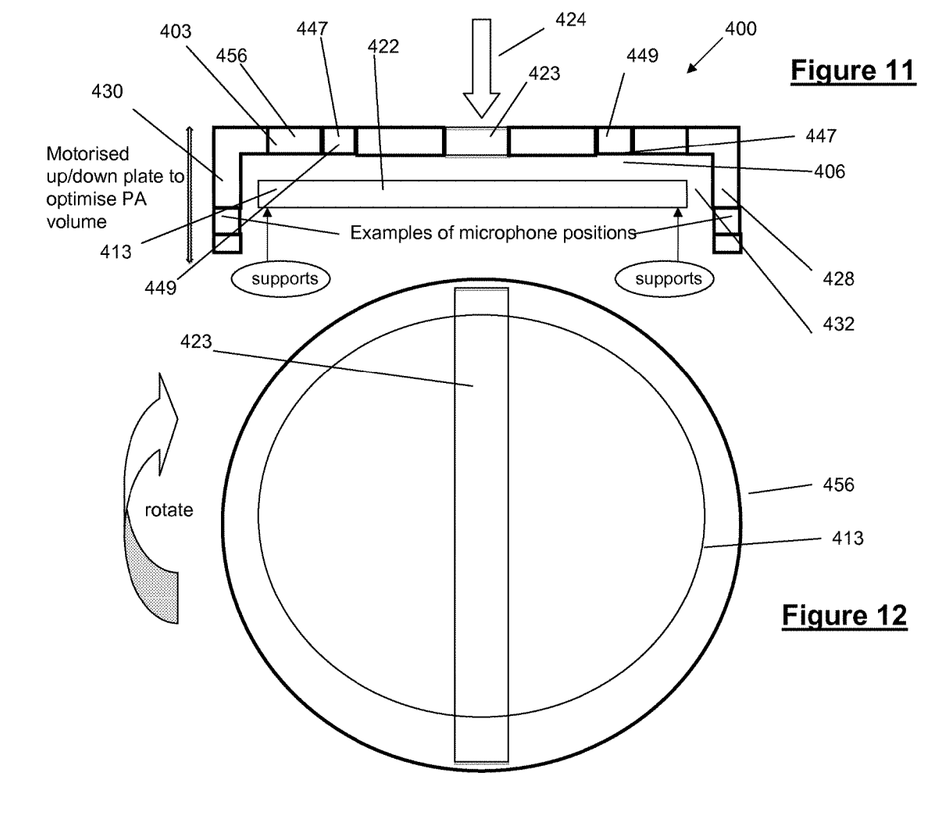
FIG. 11 is a diagrammatic view of a further inspection device.
FIG. 12 is a plan view of the device of FIG. 11.

Referring now to FIG. 10, another embodiment of an inspection device 300 is illustrated, The device 300 is substantially similar to the device 100, with like components identified by similar reference numerals, The main difference between the device 300 and the device 100 is that the device 300 includes an acoustic baffle for limiting the escape of acoustic energy from the cell 106. The baffle extends outwardly from the receiving member 103 at respective opposite sides of the wafer 113. In an exemplary arrangement, the baffle includes peaks and troughs, or similar roughened surfaces, which act as sound barriers, Referring now to FIGS. 11 and 12, another embodiment of a wafer inspection device 400 is illustrated. The device 400 comprises a receiving member 403 which defines an open cell 406 defined between a circular roof 456 and a circular stand 428 depending downwardly from the outer circumference of the roof 456. In normal operation, the roof 456 is substantially planar with a horizontal plane. The stand 428 is axially moveable such that it is retractable and extendible for facilitating varying the dimensions of the cell 406. A target wafer 413 is loaded to the cell 406 on a loading mechanism such that an upper major surface 422 thereof is substantially parallel with the horizontal plane. The dimensions of the wafer 413 are less than the dimensions of the cell 406 such that a gap 432 is provided between the wafer 413 and the receiving member 403. In this exemplary embodiment, the diameter of the roof 456 is greater than the diameter of the circular wafer 413. An elongated transparent window 423 is provided on the roof 456 for facilitating exciting the target wafer 413 located in the cell 406 with light from a laser source 424 positioned above the window 423. Microphones 449 are located in acoustic channels 447 formed in the roof 456 and are in acoustic communication with the cell 405. Otherwise, the device 400 operates in a similar fashion to the device 100.

The inspection devices as described in the present application provide a flexible, low cost, non-destructive and highly sensitive metrology tool with ultra-fast imaging speed for in-line characterization of surface and sub-surface defects within advanced semiconductor devices. Such defects are typically located anywhere from a few to several hundred microns beneath the surface and are often covered by optically opaque multi-layer structures. It is difficult to detect such defects non-invasively using conventional inline metrology tools based on optical methods. The inspection devices of the present application facilitate non-contact investigation of large area semiconductor wafers and similar samples. Wafers may be tested non-destructively in real time without the need for additional gases. However, if required the devices may be housed in a chamber which contains gases other than air. These gases may include helium or argon or other suitable gases, which may be used to enhance the photoacoustic signals. The open cell design enables straightforward wafer insertion and positioning.

It will be understood that what has been described herein are exemplary wafer inspection devices. While the present application has been described with reference to exemplary arrangements it will be understood that it is not intended to limit the teaching of the present application to such arrangements as modifications can be made without departing from the spirit and scope of the application.

Similarly the words comprises/comprising when used in the specification are used to specify the presence of stated features, integers, steps or components but do not preclude the presence or addition of one or more additional features, integers, steps, components or groups thereof.

The invention claimed is:

1. An inspection device comprising:
 a receiving member defining an open cell having two or more open sides configured to receive a moving target under test,
 an optical excitation input in optical communication with the cell for exciting a target region of the target under test,
 at least one microphone located within an acoustic channel formed in the receiving member and forming an acoustic pickup in acoustic communication with the cell for picking up acoustic energy resultant from excitation of the target, and
 a recorder for recording the acoustic energy picked up from the acoustic pickup for facilitating structural analysis of the target,
 wherein the receiving member comprises an upper jaw and a spaced apart lower jaw, the cell being defined between the upper and lower jaws, such that the target under test is free from contact from the upper and lower jaws.

2. The device of claim 1, wherein two or more acoustic pickups are provided.

3. The device of claim 2, wherein the acoustic pickups extend radially from a target point on the receiving member.

4. The device of claim 3, wherein each acoustic pickup comprises an acoustic channel formed in the receiving member for accommodating a microphone therein.

5. The device of claim 4, wherein the acoustic channel is of circular cross section.

6. The device of claim 4, wherein the diameter of the acoustic channel is non-uniform.

7. The device of claim 6, wherein the diameter of the acoustic channel progressively increases from the target point.

8. The device of claim 7, wherein the optical excitation input is in registration with the target point.

9. The device of claim 4, wherein a microphone is located in the acoustic channel.

10. The device of claim 9, wherein the microphone is moveable axially within the acoustic channel.

11. The device of claim 9, wherein the microphone is housed in a tubular member.

12. The device of claim 1, wherein the receiving member is configured for adjusting the dimensions of the cell.

13. The device of claim 1, further comprising a loading mechanism for loading a target region of the target into the cell.

14. The device of claim 13, wherein the loading mechanism is configured to rotate the target.

15. The device of claim 13, wherein the receiving member is provided in a modular arrangement for facilitating varying the dimensions of the cell.

16. The device of claim 1, wherein the receiving member comprises a plurality of cells for accommodating respective wafers therein.

17. The device of claim 16, wherein the dimensions of at least two cells are different.

18. The device of claim 1, wherein the upper and lower jaws are operably coupled together at their respective proximal ends and together define an internal arcuate surface.

19. The device of claim 1, wherein the upper and lower jaws are rectangular when viewed in plan elevation.

20. The device of claim 1, wherein each jaw comprises a distal end and a proximal end with sides extending there between.

21. The device of claim 20, wherein the upper jaw has a length of between 81.5 mm to 90 mm.

22. The device of claim 20, wherein the lower jaw has a length of between 81.5 mm to 90 mm.

23. The device of claim 20, wherein access to the cell is provided by openings adjacent the distal ends and the two sides of the receiving member.

24. The device of claim 23, wherein the proximal ends of the receiving member is closed.

25. The device of claim 13, wherein the loading mechanism is configured for loading the target region of the target into the cell via three open sides of the receiving member.

26. The device of claim 13, wherein the loading mechanism is configured to load the target to the receiving member such that an upper major surface thereof is co-planar with a horizontal plane.

27. The device of claim 1, wherein at least one acoustic pick up is located above the target when the target is loaded in the cell.

28. The device of claim 1, wherein at least one acoustic pick up is located below the target when the target is loaded in the cell.

29. The device of claim 1, wherein at least one acoustic pick up is aligned with an edge of the target when the target is loaded in the cell.

30. The device of claim 1, wherein the target comprises a substrate.

31. The device of claim 1, wherein the target comprises a semiconductor wafer.

32. The device of claim 1, wherein the target is carried on a carrier member.

33. The device of claim 1, wherein the optical excitation input comprises a laser light source.

34. The device of claim 33, wherein the laser light source is suitable for facilitating scanning the target with light.

* * * * *